United States Patent
Shinke et al.

(10) Patent No.: US 11,273,108 B2
(45) Date of Patent: Mar. 15, 2022

(54) EMULSION COSMETIC

(71) Applicant: SHISEIDO COMPANY, LTD., Tokyo (JP)

(72) Inventors: Mayo Shinke, Kanagawa (JP); Shoko Ogawa, Kanagawa (JP); Tomo Osawa, Kanagawa (JP); Tomoko Ikeda, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/765,695

(22) PCT Filed: Nov. 6, 2018

(86) PCT No.: PCT/JP2018/041235
§ 371 (c)(1),
(2) Date: May 20, 2020

(87) PCT Pub. No.: WO2019/107089
PCT Pub. Date: Jun. 6, 2019

(65) Prior Publication Data
US 2020/0405601 A1 Dec. 31, 2020

(30) Foreign Application Priority Data
Nov. 28, 2017 (JP) .............................. JP2017-228457

(51) Int. Cl.
*A61K 8/29* (2006.01)
*A61K 8/19* (2006.01)
*A61K 8/893* (2006.01)
*A61K 8/898* (2006.01)
*A61K 8/92* (2006.01)
*A61Q 1/12* (2006.01)

(52) U.S. Cl.
CPC ............... *A61K 8/29* (2013.01); *A61K 8/19* (2013.01); *A61K 8/893* (2013.01); *A61K 8/898* (2013.01); *A61K 8/92* (2013.01); *A61Q 1/12* (2013.01)

(58) Field of Classification Search
None
See application file for complete search history.

(56) References Cited

U.S. PATENT DOCUMENTS

2011/0027213 A1    2/2011  Kamel et al.
2019/0117531 A1*   4/2019  Nishida .................... A61K 8/26

FOREIGN PATENT DOCUMENTS

| JP | WO 97/30934 | 8/1997 |
| JP | 2004-182729 | 7/2004 |
| JP | 2006-028087 | 2/2006 |
| JP | 2007-277167 | 10/2007 |
| JP | 2007-277415 | 10/2007 |
| JP | 3007-302800 | 11/2007 |
| JP | 2008-184399 | 8/2008 |
| JP | 2009-179606 | 8/2009 |
| JP | 2010-163375 | 7/2010 |
| JP | 2011-026485 A | 2/2011 |
| JP | 2013-49658 | 3/2013 |
| JP | 2016-060720 | 7/2016 |
| JP | 2019-006715 | 1/2019 |
| WO | 2005-53736 | 3/2005 |
| WO | WO 2017/209077 | 12/2017 |

OTHER PUBLICATIONS

PCT/JP2018/041235, International Search Report and Written Opinion dated Feb. 5, 2019, 8 pages—Japanese, 4 pages—English.
Database WPI, Week 201633, Thomson Scientific, London, GB; AN 2016-25419M & JP 2016 060720 A (Narisu KeshohnKK) Apr. 25, 2016 (Apr. 25, 2016).
Database WPI, Week 200615, Thomson Scientific, London, GB: AN 2006-140396 & JP 2006 028087 A (Hoyu KK), Feb. 2, 2006 (Feb. 2, 2006).
EP 17806632.0, Extended European Search Report dated Dec. 10, 2019, 7 pages—English.

* cited by examiner

*Primary Examiner* — Melissa L Fisher
(74) *Attorney, Agent, or Firm* — Andrew F. Young; Nolte Lackenbach Siegel

(57) ABSTRACT

An elastomer improves the feel of inorganic powder on the skin. An emulsion cosmetic is characterized by containing: (A) 0.5-20 mass % of an inorganic powder having an elastomer coating layer containing (a1) and (a2); and (B) 20-80 mass % of an oil component. The elastomer is characterized by comprising: (a1) a silicone polymer having an amino group; and (a2) a carboxyl group-containing silicone polymer or a carboxyl group-containing acrylic polymer, wherein the molar ratio of the amino group to the carboxyl group, Y/X is in the range of 0.1-1.2 (Y is the molar amount of the carboxyl group contained in the component (a2), and X is the molar amount of the amino group contained in the component (a1)).

6 Claims, No Drawings

EMULSION COSMETIC

CROSS REFERENCE TO RELATED APPLICATIONS

This application relates to and claims priority from PCT Ser. No.:PCT/JP2018/041235 filed Nov. 6, 2018, the entire contents of which is incorporated herein by reference. This application also claims the priority of Japanese Patent Application No. 2017-228457 filed on Nov. 28, 2017, which is incorporated herein by reference.

FIELD OF THE INVENTION

The present invention relates to an emulsion cosmetic and particularly relates to an improvement of in-use feel on the skin, and an improvement of concealability while maintaining a natural finish when the emulsion cosmetic is applied to the skin, due to the use of an elastomer-coated inorganic powder.

BACKGROUND OF THE INVENTION

Powders for makeup cosmetics such as foundation and makeup base are treated in various ways to provide the functions required for the makeup cosmetics.

For example, a powder is known in which the surface of a base powder is coated with a hydrophobizing agent and a polymer containing acrylamide monomers, having a specific structure (such as 11-methacrylamidoundecanoic acid), as a composition monomer thereof in order to achieve high hydrophobicity and improve washability (Patent Literature 1).

Concerning attempts to provide a powder cosmetic, in particular a powder makeup cosmetic such as foundation or makeup base, which has a high ability to allow makeup to last longer (prevent makeup from coming off), it is known that the incorporation of a particular treated powder provides a powder makeup cosmetic having a high ability to allow makeup to last longer (prevent makeup from coming off) (Patent Literature 2).

CITATION LIST

Patent Literature

[Patent Literature1] Japanese Patent Publication No. 2007-277167
[Patent Literature2] Japanese Patent Publication No. 2008-184399

DISCLOSURE OF THE INVENTION

Problem to be Solved by the Invention

However, a treated inorganic powder as taught in Patent Literature 1 or 2 has a problem in that when an emulsion cosmetic containing the treated inorganic powder is applied to skin, the cosmetic may give frictional feel and unpleasant powdery sense to the skin.

The present invention has been made in view of such circumstances, and an object of the present invention is to improve the skin sense of an emulsion cosmetic along with imparting moisture and eliminating a powdery sense due to the use of an inorganic powder, the surface of which is coated with a specific elastomer. And another object of the present invention is to provide an emulsion cosmetic having excellent concealability while maintaining a natural finish when applied to the skin.

Means to Solve the Problem

As a result of intensive investigations aimed at solving the above problem, the present inventors coated an inorganic powder using a composition having elastomeric properties prepared by combining an amino group-containing silicone polymer (with a carboxyl group-containing silicone polymer or a carboxyl group-containing acrylamide polymer. The present inventors have found that an emulsion cosmetic attains improved skin senses and moistening senses with non-powdery feel due to the use of the inorganic powder coated with the elastomer in the emulsion cosmetic. Moreover, the present inventors have also found that the cosmetic has excellent concealability while maintaining a natural finish when applied to the skin. The present inventors have completed the present invention based on these findings.

The emulsion cosmetic according to the present invention comprises:
(A) 0.5 to 20% by mass of an inorganic powder having an elastomer-coated layer containing (a1) and (a2) below; and
(B) 20 to 80% by mass of an oil component,
wherein the elastomer comprises:
(a1) an amino group-containing silicone polymer; and
(a2) a carboxyl group-containing silicone polymer or a carboxyl group-containing acrylamide polymer,
wherein a molar ratio Y/X between amino groups and carboxyl groups is within a range of 0.1 to 1.2, wherein Y denotes the molar amount of carboxyl groups contained in the component (a2), and X denotes the molar amount of amino groups contained in the component (a1).

It is preferable that in the emulsion cosmetic, the amount of the elastomer is 0.5 to 20% by mass relative to the amount of the inorganic powder.

It is preferable that in the emulsion cosmetic, silicone oil (b1) accounts for 50% by mass or more of the oil component in the cosmetic.

It is preferable that in the emulsion cosmetic, the silicone oil (b1) is one or more selected from chain polysiloxanes and cyclic polysiloxanes.

It is preferable that in the emulsion cosmetic, polar oil (b2) accounts for 50% by mass or more of the oil component in the cosmetic.

It is preferable that in the emulsion cosmetic, the polar oil (b2) is one or more selected from glyceryl tri(2-ethylhexanoate), pentaerythrityl tetraethylhexanoate, cetyl 2-ethylhexanoate, and isododecyl neopentanoate.

In the emulsion cosmetic,
the component (a1) is an amino group-containing silicone polymer represented by the general formula (1); and
(a2) is a carboxyl group-containing silicone polymer represented by the general formula (2) or a carboxyl group-containing acrylamide polymer represented by the general formula (3), wherein the elastomer comprises:
(A) an amino group-containing silicone polymer represented by the following formula (1):

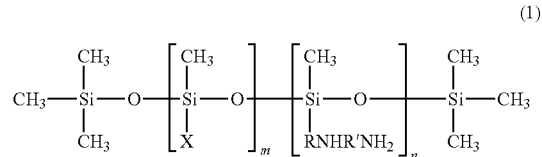

wherein X is an alkyl group having 1 to 18 carbons, and R and R are an alkyl group; and (B) a carboxyl group-containing silicone polymer represented by the following general formula (2):

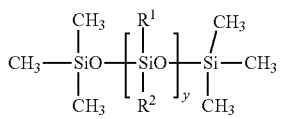
(2)

wherein $R^1$ and $R^2$ are a methyl group or a group represented by the following formula (4), the total number of the groups $R^1$ and $R^2$ is 1 to 100 per molecule, and y represents an integer of 1 to 50000:

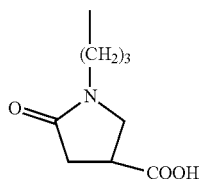
(4)

or
a carboxyl group-containing acrylamide polymer represented by the following general formula (3):

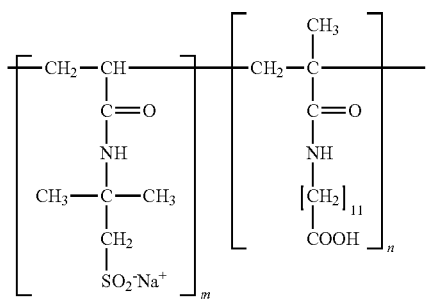
(3)

wherein
a molar ratio Y/X between amino groups and carboxyl groups is 0.1 to 1.2, wherein Y denotes the molar amount of carboxyl groups contained in the component (B), and X denotes the molar amount of amino groups contained in the component (A).

Effect of the Invention

According to the present invention, the emulsion cosmetic attains improved skin senses and moistening senses with non-powdery feel due to the use of an inorganic powder having an elastomer-coated layer in the emulsion cosmetic. Moreover, a cosmetic that has excellent concealability while maintaining a natural finish when applied to the skin can be provided.

BEST MODE FOR CARRYING OUT THE INVENTION

Hereinafter, the present invention will be described in detail.
(A) Inorganic Powder Having Elastomer-Coated Layer
The inorganic powder having an elastomer-coated layer used in the present invention is obtained by coating the surface of talc with an elastomer produced by mixing (a1) an amino group-containing silicone polymer and (a2) a carboxyl group-containing silicone polymer and heating the resulting mixture. The constitutional components (a1) and (a2) of the elastomer used in the present invention will be described first.
(a1) Amino Group-Containing Silicone Polymer
The amino group-containing silicone polymer (a1) used in the present invention is a side chain amino-modified silicone represented by the following general formula (1).

[General Formula 1]

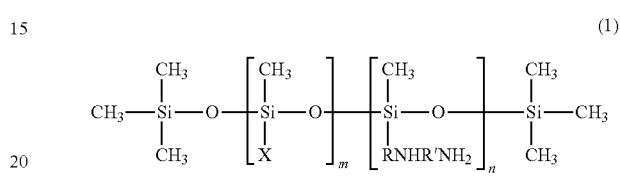
(1)

wherein X is an alkyl group having 1 to 18 carbons, and R and R' are respectively an alkyl group.

In the general formula (1), m is preferably 20 to 2000 to provide the elastomer with a suitable hardness. Whereas, when m is less than 20, the elastomer may not be formed, and when m is more than 2000, handling and production thereof may become difficult, so that the results are not preferable.

In the general formula (1), n is preferably 1 to 100 to provide the elastomer with a suitable hardness. Whereas, when n is less than 1, the elastomer may not be formed and when n is more than 100, the elastomer may be excessively hard, so that the results may not be preferable.

In the general formula (1), R is suitably an alkyl chain, and particularly, a propyl group is preferred in terms of mass production efficiency.

In the general formula (1), R' is suitably an alkyl chain, and particularly, an ethyl group is preferred in terms of mass production efficiency.

The amino group equivalent of the amino group-containing silicone polymer (a1) is preferably 500 g/mol to 20000 g/mol to provide the resulting elastomer with a suitable hardness. Whereas when the amino group equivalent is less than 500, the elastomer may be excessively hard, and when the amino group equivalent is more than 20000, the elastomer may not be formed, so that the results are not preferable.

Examples of commercially-available products of the amino group-containing silicone polymer (a1) include: KF-8004, KF-8005S, and KF-867S (available from Shin-Etsu Chemical Co., Ltd.); XF42-B1989 (available from Momentive Performance Materials Inc.); ADM 1650 and ADM 1370 (available from Wacker Asahikasei Silicone Co., Ltd.); and SF 8452C and SS 3551 (available from Dow Corning Toray Co., Ltd.).

The "amino group equivalent" refers to a value indicating the weight of an amino group-containing substance per mole of amino groups.
(a2) Carboxyl Group-Containing Silicone Polymer and Carboxyl Group-Containing Acrylamide Polymer
The carboxyl group-containing silicone polymer (a2) used in the present invention is a side chain carboxyl-modified silicone having a carboxyl group equivalent of 1000 g/mol to 40000 g/mol and represented by the general formula (2) below.

The carboxyl group-containing acrylamide polymer (a2) used in the present invention is a side chain carboxyl-modified acrylamide polymer having a carboxyl group equivalent of 200 g/mol to 1000 g/mol and represented by the general formula (3) below.

The "carboxyl group equivalent" refers to a value indicating the weight of a carboxyl group-containing substance per mole of carboxyl groups.

The general formula (2) is represented by the following (2) and formula (3).

[Formula (2)]

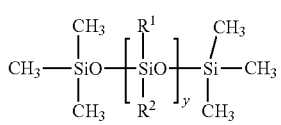
(2)

wherein R1 and R2 each denote a methyl group or a group represented by the following formula (3) below, the number of the groups is 1 to 100 per molecule, and y represents an integer of 1 to 50000.

[Formula 3]

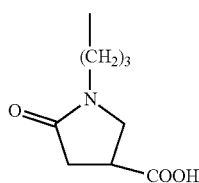
(4)

The general formula (3) is represented by the following formula 4.

[Formula 4]

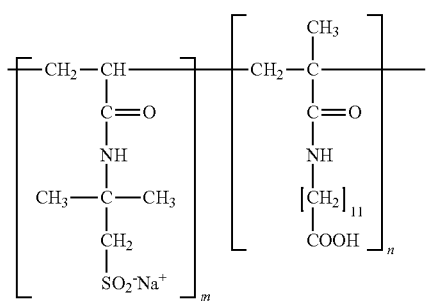
(3)

wherein m/(m+n)=0 to 0.5.

Examples of commercially-available products of the carboxyl group-containing silicone polymer represented by the general formula (2) include SENSASIL PCA (available from Croda, Inc.).

The carboxyl group-containing acrylamide polymer represented by the general formula (3) can be synthesized using a known method.

A specific example is 12-methacrylamidododecanoic acid (MAD)/2-acrylamido-2-methylpropanesulfonic acid (AMPS) copolymer (90/10), which was synthesized as follows.

18.50 g (65.37 mmol) of 12-methacrylamidododecanoic acid (MAD), 1.50 g (7.24 mmol) of 2-acrylamido-2-methylpropanesulfonic acid (AMPS, available from Sigma-Aldrich Japan K.K.), 0.29 g (7.25 mmol) of sodium hydroxide, and 0.30 g (1.83 mmol) of azobisisobutyronitrile (available from Nacalai Tesque, Inc.) were dissolved in 60.0 g of methanol. The azobisisobutyronitrile was recrystallized from methanol according to an ordinary method before use. The solution was degassed by bubbling with argon for 60 minutes, after which the container containing the solution was capped with a septum and heated at 60° C. for 20 hours to allow polymerization to proceed. After the completion of the polymerization reaction, the reaction solution was added dropwise into a largely excessive amount of diethyl ether, and the resulting precipitate was collected by suction filtration. The collected precipitate was then dried under reduced pressure to give 15.2 g of a random MAD/AMPS copolymer (90/10) (yield: 75.1%). The weight-average molecular weight was 50000.

The carboxyl group equivalent of the component (a2) is preferably 200 to 40000, because in this case the resulting elastomer has a suitable hardness. It is not preferable that the carboxyl group equivalent be less than 200, because in this case the elastomer may be excessively hard. It is not preferable that the carboxyl group equivalent be more than 40000, because in this case the elastomer may not be formed.

A molar ratio Y/X between amino groups of the amino group-containing silicone polymer (a1) and carboxyl groups of the carboxyl group-containing silicone polymer or carboxyl group-containing acrylamide polymer (a2) must be 0.1 to 1.2, wherein Y denotes the molar amount of carboxyl groups contained in the component (a2), and X denotes the molar amount of amino groups contained in the component (a1). This ratio is more preferably 0.1 to 0.8. It is not preferable that the ratio be less than 0.1, because in this case the elastomer may not be formed. It is not preferable that the ratio be more than 1.2, because in this case the elastomer may not be formed.

The elastomer is coated on the surface of talc. When talc coated with the elastomer is used in a cosmetic, the cosmetic attains improved skin senses and moistening senses with non-powdery feel. Moreover, a cosmetic having excellent concealability while maintaining a natural finish when applied to the skin can be obtained.

The amount of the elastomer with which the inorganic powder is coated is 0.5 to 20% by mass, more preferably 1 to 15% by mass, relative to the amount of the inorganic powder. It is not preferable that the amount of the elastomer to be incorporated be more than 20% by mass, because in this case fusing of the inorganic powder or decrease in formability of the emulsion cosmetic may occur. It is not preferable that the amount of the elastomer to be incorporated be less than 0.5% by mass, because in this case the feel-improving effect may not be obtained.

The amount of the inorganic powder having an elastomer-coated layer to be incorporated is 0.5 to 20% by mass and more preferably 2 to 20% by mass relative to the emulsion cosmetic. It is not preferable that the amount of the inorganic powder to be incorporated be more than 20% by mass because in this case there may be resistance to the spreading of the emulsion cosmetic. It is not preferable that the amount of the inorganic powder to be incorporated be less than 0.5% by mass because in this case the effect of improving the in-use feel may not be obtained.

The inorganic powder to be coated with the elastomer is selected from powder materials usable in cosmetics. In particular, talc, mica, sericite, kaolin, titanium dioxide, iron oxide, zinc oxide, and the like are preferably used.

Examples of commercially available products of talc include JET-R series (available from ASADA MILLING CO., LTD.), Micro Ace series (available from NIPPON TALC CO., LTD.), and FL108, FG106, MG115 and RL217 available from FUJI TALC INDUSTRIAL CO., LTD. Examples of commercially available products of mica include PDM-9WA (available from TOPY INDUSTRIES, LTD.).

The inorganic powder having an elastomer-coated layer (A) used in the present invention can be obtained through a step of mixing talc with the amino group-containing silicone polymer (a1) and a step of adding the carboxyl group-containing silicone polymer (a2) and heating the resulting mixture.

The inorganic powder having an elastomer-coated layer (A) can be obtained by a known method of producing a coated powder. Specifically, for example, talc and the amino group-containing silicone polymer (a1) are placed in a Henschel mixer and mixed at a low speed for 10 minutes. The carboxyl group-containing silicone polymer (a2) is then added, followed by mixing at a low speed for 10 minutes and then by heating. In this manner, elastomer-coated talc usable in the present invention can be obtained.

The order of addition of the component (a1) and component (a2) may be reversed to obtain the inorganic powder having an elastomer-coated layer usable in the present invention.

(B) Oil Component

It is essential to the present invention that an oil component (B) is incorporated. Examples of the oil component include silicone oil, polar oil, ester oil, hydrocarbon oil, fatty acid, and higher alcohol. In particular, silicone oil and polar oil are suitably used.

The amount of the oil component to be incorporated is not particularly limited, and is preferably 20 to 80% by mass.

(b1) Silicone Oil

In the present invention, silicone oil is suitably used. Examples of the silicone oil include chain polysiloxanes (e.g., dimethyl polysiloxane, methylphenyl polysiloxane, and diphenyl polysiloxane); cyclic polysiloxanes (e.g., octamethylcyclotetrasiloxane, decamethylcyclopentasiloxane, and dodecamethylcyclohexasiloxane), silicone resins having a three-dimensional network, silicone rubbers, various modified polysiloxanes (amino-modified polysiloxane, polyether-modified polysiloxane, alkyl-modified polysiloxane, and fluorine-modified polysiloxane).

When the amount of the silicone oil (b1) to be incorporated is 50% by mass or more and more preferably 60% by mass or more in the entirety of oil components of the emulsion cosmetic, a fresh, smoothly spreadable cosmetic that does not have powderiness can be obtained. An amount to be incorporated less than 50% by mass is not preferable because in this case the effect of improving the in-use feel may not be obtained.

Examples of commercially available products of the silicone oil (b1) include Execol D-5 (available from Shin-Etsu Chemical Co., Ltd.), Silicone KF-96L-1.5CS (available from Shin-Etsu Chemical Co., Ltd.), and Silicone KF-96A-6T (available from Shin-Etsu Chemical Co., Ltd.).

(b2) Polar Oil Component

A polar oil component is suitably used in the present invention. The polar oil component refers to an oil component having an IOB value of 0.05 to 0.80.

Examples of the polar oil component include 2-ethylhexyl paramethoxycinnamate (IOB value: 0.28), 2-ethylhexyl 2-cyano-3,3-diphenylacrylate (IOB value: 0.33), tripropylene glycol dipivalate (IOB value: 0.52), cetyl octanoate (IOB value: 0.13), trimethylolpropane tri(2-ethylhexanoate) (IOB value: 0.31), pentaerythritol tetra(2-ethylhexanoate) (IOB value: 0.35), alkyl benzoate (C12 to C15) (IOB value: 0.19), glyceryl tri(caprylate/caprate) (IOB value: 0.36), phenethyl benzoate (MB value: 0.30), propylene glycol di(caprylate/caprate) (MB value: 0.32), di(2-ethylhexyl) succinate (MB value: 0.32), trioctanoin (MB value: 0.36), glyceryl tri(2-ethylhexanoate) (MB value: 0.36), glyceryl tri(2-ethylhexanoate), and sorbitan sesquiisostearate.

When the amount of the polar oil component (b2) to be incorporated is 60% by mass or more in the entirety of oil components of the emulsion cosmetic, the resulting cosmetic does not have resistance to being spread while providing an elastic feel and does not have powderiness. An amount to be incorporated less than 60% by mass is not preferable because in this case the effect of improving the in-use feel may not be obtained.

Examples of commercially available products of the polar oil component (b2) include RA-G-308 (available from Nippon Fine Chemical Co., Ltd.), RA-PE-408 (available from Nippon Fine Chemical Co., Ltd.), CIO (available from Nippon Surfactant Industries Co., Ltd.), and isododecyl pivalate (available from Kokyu Alcohol Kogyo Co., Ltd.).

Other than the inorganic powder having an elastomer-coated layer (A) and the oil component (B) used in the present invention, an inorganic powder and an organic powder that are usable in cosmetics may be incorporated.

Examples of inorganic powder include sericite, natural mica, calcined mica, integrated mica, integrated sericite, alumina, mica, kaolin, bentonite, smectite, calcium carbonate, magnesium carbonate, calcium phosphate, anhydrous silicic acid, magnesium oxide, tin oxide, iron oxide, yttrium oxide, chromic oxide, titanium dioxide, zinc oxide, cerium oxide, aluminum oxide, magnesium oxide, chromium hydroxide, Prussian blue, ultramarine, calcium phosphate, aluminium hydroxide, barium sulfate, magnesium sulfate, silicic acid, magnesium aluminum silicate, silicic acid calcium, silicic acid barium, magnesium silicate, aluminum silicate, silicic acid strontium, silicon carbide, magnesium fluoride, tungstic acid metal salt, magnesium aluminate, magnesium aluminometasilicate, chlorohydroxy aluminum, clay, zeolite, hydroxy apatite, ceramic powder, spinel, mullite, cordierite, aluminum nitride, titanium nitride, silicon nitride, a lantern, samarium, tantalum, terbium, europium, neodymium, Mn—Zn ferrite, Ni—Zn ferrite, silicone carbide, titanic acid cobalt, barium titanate, titanic acid iron, lithium cobalt chitanate, aluminic acid cobalt, antimony containing tin oxide, tin containing indium oxide, magnetite, aluminum powder, gold powder, silver powder, platinum powder, copper powder, noble metal colloid, iron powder, zinc powder, cobalt blue, cobalt violet, cobalt green, lower titanium dioxide, titanium dioxide particulate, butterfly-like barium sulfate of, petal-like zinc oxide, tetrapod-like zinc oxide, and zinc oxide particulate. Examples of pearled pigments include mica coated with titanium dioxide, synthetic mica coated with titanium dioxide, silica coated with titanium dioxide, integrated mica coated with titanium dioxide, talc coated with titanium dioxide, silica coated with zinc oxide, pigmentation mica coated with titanium dioxide, mica titanium coated with red oxide, mica titanium coated with red ocher and black iron oxide, mica titanium coated with carmine, and mica titanium coated with iron blue pigments.

Among these, mica, sericite, kaolin, titanium dioxide, iron oxide, zinc oxide and the like are preferably used.

Examples of commercially-available products of the inorganic powder include: IRIODIN® series, TIMIRON® series, COLORONA® series, DICHRONA® series, XIRONA® series, and RONASTAR® series of MERCK KGaA; DESERTREFLECTIONS series, TIMICA series, FLAMENCO series, CLOIZONNE series, DUOCROME series, GEMTONE series, CELLINI series, MEARLMAID series, REFLECKS series, CHROMA-LITE series, and COSMICA series of BASF SE; PRESTIGE® series, VISIONAIRE® series, and MIRAGE series of ECKART GmbH; METASHINE® of Nippon Sheet Glass Co. Ltd.; PROMINENCE® of NIHON KOKEN KOGYO CO., LTD.; Cosmetica White Pearl series and Sharon Pearl series of CQV Co., Ltd.; and Precioso White Peartescent Pigments of Taizu. Other examples of the inorganic powder include: effect pigments such as aluminum flakes, silica flakes, alumina flakes, and glass flakes; colcothar-coated mica; carmine; titanium dioxide-coated sodium/calcium borosilicate; titanium dioxide-coated calcium/aluminum borosilicate; bismuth oxychloride; fish scale flakes; stainless steel powder; tourmaline powder; powders obtained by crushing precious stones such as sapphire and ruby; mango violet; glass fibers; carbon fibers; silicon carbide fibers; alumina fibers; β-wollastonite; Zonolite; potassium titanate fibers; aluminum borate fibers; basic magnesium sulfate fibers; and silicon nitride fibers.

Examples include: organic powders such as silicone elastomer powder, silicone powder, silicone resin-coated silicone elastomer powder, polyamide resin powder (nylon powder), polyethylene powder, polymethyl methacrylate powder (such as methyl methacrylate crosspolymer), polystyrene powder, styrene-acrylic acid copolymer resin powder, benzoguanamine resin powder, polytetrafluoroethylene powder, and cellulose powder; organic pigments such as zirconium lakes, barium lakes, and aluminum lakes (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404).

<Production Method>

The emulsion cosmetic containing an inorganic powder having an elastomer-coated layer of the present invention can be obtained through a step of adding oil phase components and mixing a powder therewith by a homomixer or the like, and a step of emulsifying the resulting oil phase components with aqueous phase components by a homomixer or the like.

According to the technique of the present invention, elastomer coating can be applied collectively to all of the inorganic powder and the organic powder to be incorporated in a cosmetic, and then other oil components can be added to obtain the cosmetic. Specifically, all of the inorganic powder and organic powder to be incorporated in the cosmetic are mixed in advance, the elastomer-forming oil components are added to the resulting powder mixture, the powder mixture is heated together with the elastomer-forming oil components to obtain an elastomer-coated powder mixture, and then this mixture may then be used in the emulsion cosmetic.

If a step of adding the elastomer-forming oil components (a1) and (a2) used in the technique of the present invention together with the other oil components and then performing heating is employed, the functions intended by the present invention cannot be obtained.

Specifically, when the inorganic powder and the organic powder to be incorporated in the cosmetic are mixed, then a mixture of the components (a1) and (a2) and other oil components are added thereto, and the mixture is heated, the resulting cosmetic is inferior in-use feel and concealability.

The oil components other than the components (a1), (a2) and (B) can be incorporated without qualitative or quantitative limitations as long as the effect of the present invention is not impaired. A liquid oil, a solid oil, a wax, a hydrocarbon, a higher fatty acid, a higher alcohol, an ester, a moisturizer, a water-soluble polymer, a thickener, a film former, an ultraviolet absorber, a metal sequestrant, a lower alcohol, a polyhydric alcohol, a sugar, an amino acid, an organic amine, a polymer emulsion, a pH adjuster, a nutritional supplement for skin, an antioxidant, an antioxidant synergist, and/or a flavor may be incorporated as necessary. The cosmetic can be produced by an ordinary method appropriate for the intended form of the cosmetic.

Examples of liquid fats include avocado oil, camellia oil, turtle oil, macadamia nut oil, corn oil, mink oil, olive oil, rapeseed oil, egg yolk oil, sesame oil, par chic oil, wheat germ oil, sasanqua oil, castor oil, linseed oil, safflower oil, cotton seed oil, perilla oil, soybean oil, groundnut oil, brown real oil, torreya oil, rice bran oil, Chinese wood oil, Japanese tung oil, jojoba oil, germ oil, and triglycerol.

Examples of solid fats include cacao butter, coconut oil, horse fat, hydrogenated coconut oil, palm oil, beef fat, mutton suet, hydrogenated beef fat, palm kernel oil, lard, beef bones fat, Japan wax kernel oil, hardened oil, hoof oil, Japan wax, and hydrogenated castor oil.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and, POE hydrogenated lanolin alcohol ether.

Examples of hydrocarbon oils include liquid paraffin, ozocerite, squalene, pristane, paraffin, ceresin, squalane, Vaseline®, and microcrystalline wax.

Examples of moisturizers include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salts, dl-pyrrolidone carboxylates, alkylene oxide derivatives, short-chain soluble collagen, diglycerin (EO)PO adduct, chestnut rose extract, yarrow extract, and melilot extract.

Examples of ultraviolet light absorbers include benzoic acid family ultraviolet light absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid family ultraviolet light absorbers (for example, homomenthyl N-acetylanthranilate); salicylic acid family ultraviolet light absorbers (for example, amyl salicylate, menthyl salicylate, homomenthyl salicylate, octyl salicylate, phenyl salicylate, benzyl salicylate, and p-isopropanolphenyl salicylate); cinnamic acid family ultraviolet light absorbers (for example, octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β- phenylcinnamate, 2-ethylhexyl α-cyano-β-phenylcinnamate, and glyceryl mono-2-ethylhexanoyl-diparamethoxy cinnamate); benzophenone family ultraviolet light absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one, dimorpholino pyridazinone; 2-ethylhexyl-2-cyano-3,3-diphenyl acrylate; and 2,4-bis{[4-(2-ethylhexyloxy)-2-hydroxy]-phenyl}-6-(4-methoxy phenyl)-(1,3,5)-triazine.

The emulsion cosmetic containing the inorganic powder having an elastomer-coated layer of the present invention can, as necessary, contain water, a powder other than the powders mentioned above, a surfactant, a lower alcohol, a polyhydric alcohol, a moisturizer, a preservative, a polymer (including a film former), an antioxidant, a flavor, and/or other various agents, without qualitative or quantitative limitations as long as the effect of the present invention is not impaired.

The emulsion cosmetic of the present invention can be in any product form, such as whitening essence, emulsion, cream, mask, makeup base, BB cream, sunscreen, foundation, lipstick, eye shadow, eye liner, mascara, face wash, spray, mousse, hair rinse, and shampoo, and is suitably used as a foundation in particular.

Also, the present invention is not limited with respect to the form of a container. For example, an absorbent may be impregnated with the cosmetic and accommodated within an air-tight compact. Examples of the absorbent include non-woven fabric made of a single or mixed material of resin, pulp, cotton or the like, a resin-treated fiber, a foam such as sponge, and a porous body having continuous pores. Examples of the absorbent material include NBR (acrylonitrile butadiene rubber), SBR (styrene butadiene rubber), NR (natural rubber), urethane, nylon, polyolefin, polyester, EVA (ethylene vinyl acetate), PVA (polyvinyl alcohol), silicon, and elastomers, but the absorbent is not limited to these materials as long as the cosmetic can be contained.

EXAMPLES

Hereinafter, the present invention will be described in detail with reference to Examples. The present invention is not limited by these Examples in any respect. The amounts of components to be incorporated are expressed by % by mass relative to the entire system in which the components are incorporated, unless otherwise specified.

Evaluation methods and criteria used in the following test will be described first.

<Elastomer Coating Test>

In this test, no separation between the original powder and the elastomer was confirmed based on visual inspection and feel to the touch. Additionally, it was also confirmed that the amount of the elastomer coating was appropriate relative to the amount of the powder charged by elemental analysis and that the coating was appropriate by floating the coated powder on water to check whether it had water repellency.

G (good): The powder is coated with the elastomer.

NG (not good): The powder is not coated with the elastomer.

First, an investigation was conducted on the amounts of the amino group-containing silicone polymer (a1) and the carboxyl group-containing silicone polymer (a2) to obtain a composition used in the present invention in the form of an elastomer.

Elastomers used in the present invention which had formulations as shown in tables below were prepared by the following production method.

<Production Method>

Each of the elastomers used in the present invention was obtained by mixing and stirring the carboxyl group-containing silicone polymer and the amino group-containing silicone polymer and heating the mixture at 105° C. for 12 hours.

First, the present inventors conducted an investigation on the molar ratio Y/X between amino groups and carboxyl groups at which the amino group-containing silicone polymer (a1) and the carboxyl group-containing silicone polymer (a2) exhibit elastomeric properties, wherein Y denotes the molar amount of carboxyl groups contained in the component (a2), and X denotes the molar amount of amino groups contained in the component (a1). The ratio Y/X is the ratio [amount (mmol) of carboxyl group]/[amount (mmol) of amino group] calculated from the carboxyl group equivalent and diamino group equivalent determined by NMR.

The formulations of the Test Examples are as shown in Table 1 and Table 2 below.

TABLE 1

| | Test Example | 1-1 | 1-2 | 1-3 | 1-4 | 1-5 | 1-6 |
|---|---|---|---|---|---|---|---|
| a1 | Aminoethylamino-propylmethylsiloxane-dimethylsiloxane copolymer (g) (*1) | 2 | 1.8 | 1.6 | 1.4 | 1.2 | 1 |
| a2 | PCA dimethicone (g) (*2) | — | 0.2 | 0.4 | 0.6 | 0.8 | 1 |
| | Y/X | | 0.03 | 0.07 | 0.12 | 0.18 | 0.27 |
| X: Molar amount of amine, | | | | | | | |
| Y: Molar amount of carboxylic acid (calculated from NMR data) | | | | | | | |
| | State | Liquid | | | Elastomer | | |

TABLE 2

| | Test Example | 1-7 | 1-8 | 1-9 | 1-10 | 1-11 |
|---|---|---|---|---|---|---|
| a1 | Aminoethylamino-propylmethylsiloxane-dimethylsiloxane copolymer (g) (*1) | 0.8 | 0.6 | 0.4 | 0.2 | — |
| a2 | PCA dimethicone (g) (*2) | 1.2 | 1.4 | 1.6 | 1.8 | 2 |
| | Y/X | 0.41 | 0.64 | 1.1 | 2.5 | |
| X: Molar amount of amine, | | | | | | |
| Y: Molar amount of carboxylic acid (calculated from NMR data) | | | | | | |
| | State | Liquid | | | Elastomer | |

(*1) KF-8004 (Shin-Etsu Chemical Co., Ltd.)

$^1$H NMR of KF-8004 was measured, and the diamine equivalent was calculated to be 3090.4 g/mol from an integral of a signal derived from $CH_3$ and an integral of a signal derived from —$CH_2$—.

(*2) SENSASIL PCA (Croda, Inc.)

$^1$H NMR of SENSASIL PCA was measured, and the carboxyl equivalent was calculated to be 5631 g/mol from an integral of a signal derived from $CH_3$ and an integral of a signal derived from $—CH_2—$.

It was found that elastomers were obtained by the formulations of Test Examples 1-4 to 1-9.

It was therefore found that the molar ratio Y/X between amino groups and carboxyl groups of 0.1 to 1.2 was advantageous.

Next, the present inventors conducted an investigation on whether a carboxyl group-containing acrylamide polymer could alternatively be used as another component (a2).

TABLE 3

|   |   | Test Example | | | | | | | |
|---|---|---|---|---|---|---|---|---|---|
|   |   | 2-1 | 2-2 | 2-3 | 2-4 | 2-5 | 2-6 | 2-7 | 2-8 |
| a1 | Aminoethylaminopropylmethylsiloxane-dimethylsiloxane copolymer (g) (*1) | 1 | 1 | 1 | 1 | 1 | 1 | 1 | 1 |
| a2 | COOH-containing acrylamide polymer (*3) | 1 | 0.5 | 0.33 | 0.25 | 0.2 | 0.17 | 0.13 | 0.1 |
|   | Y/X X: Molar amount of amine, Y: Molar amount of carboxylic acid (calculated from NMR data) | 5.0 | 2.5 | 1.7 | 1.3 | 1.0 | 0.8 | 0.6 | 0.5 |
|   | State |  | Hard solid |  |  |  | Elastomer |  |  |

(*3) The COOH-containing acrylamide polymer was obtained by the following method.

12-Methacrylamidododecanoic acid (MAD)/2-acrylamido-2-methylpropanesulfonic acid (AMPS) copolymer (90/10)

18.50 g (65.37 mmol) of 12-methacrylamidododecanoic acid (MAD), 1.50 g (7.24 mmol) of 2-acrylamido-2-methylpropanesulfonic acid (AMPS, available from Sigma-Aldrich Japan K.K.), 0.29 g (7.25 mmol) of sodium hydroxide, and 0.30 g (1.83 mmol) of azobisisobutyronitrile (available from Nacalai Tesque, Inc.) were dissolved in 60.0 g of methanol. The azobisisobutyronitrile was recrystallized from methanol according to an ordinary method before use.

The solution was degassed by bubbling with argon for 60 minutes, after which the container containing the solution was capped with a septum and heated at 60° C. for 20 hours to allow polymerization to proceed. After the completion of the polymerization reaction, the reaction solution was added dropwise into a largely excessive amount of diethyl ether, and the resulting precipitate was collected by suction filtration.

The collected precipitate was then dried under reduced pressure to give 15.2 g of a COOH-containing acrylamide polymer in the form of a random copolymer (yield: 75.1%). The weight-average molecular weight of the COOH-containing acrylamide polymer obtained was 50000.

This led to the conclusion that an elastomer used in the present invention could be obtained also with the use of a carboxyl group-containing acrylamide polymer.

<Elastomer-Coated Inorganic Powder>

As described hereinafter, the present inventors further conducted an investigation on whether various inorganic powders could be coated with an elastomer used in the present invention.

<Production Method>

An inorganic powder (C) and a carboxyl group-containing silicone polymer are placed in a Henschel mixer and mixed at a low speed for 10 minutes. An amino group-containing silicone polymer was then added, followed by mixing at a low speed for 10 minutes and then by heating. In this manner, an inorganic powder having an elastomer-coated layer used in the present invention was obtained.

TABLE 4

|   |   | Test Example | | |
|---|---|---|---|---|
|   |   | 3-1 | 3-2 | 3-3 |
| (A) | Aminoethylaminopropylmethylsiloxane-dimethylsiloxane copolymer (g) (*1) | 2 | 2 | 2 |
| (B) | PCA dimethicone (g) (*2) | 3 | 3 | 3 |

TABLE 4-continued

|   |   | Test Example | | |
|---|---|---|---|---|
|   |   | 3-1 | 3-2 | 3-3 |
| (C) | Talc | 95 | — | — |
|   | Mica | — | 95 | — |
|   | Synthetic phlogopite iron | — | — | 95 |
| Coating state |   | good | good | good |

Various Inorganic Powders Listed in Table 4

Talc: Talc JA-68R (available from ASADA MILLING CO., LTD.)

Mica: PDM-9WA (available from TOPY INDUSTRIES, LTD.)

Synthetic phlogopite iron: PDM-FE (available from TOPY INDUSTRIES, LTD.)

Test Examples 3-1 to 3-3 demonstrated that an elastomer according to the present invention could be used to coat various inorganic powders.

<Emulsion Cosmetic>

The present inventors conducted an investigation on the incorporation of an inorganic powder having an elastomer-coated layer in the emulsion cosmetic of the present invention and made evaluations of in-use feel, concealability, and the like according to the following criteria.

<Concealability>

Ten experienced panelists evaluated the concealability of each of the compositions of Test Examples that the panelists felt when placing the composition on their palm and applying it to their skin. The compositions were rated according to the following criteria.

A: Nine or more of the ten panelists reported that the concealability was good.

B: Seven or more and less than nine of the ten panelists reported that the concealability was good.

BC: Five or more and less than seven of the ten panelists reported that the concealability was good.

C: Three or more and less than five of the ten panelists reported that the concealability was good.

D: Less than three of the ten panelists reported that the concealability was good.

<Smoothness>

Ten experienced panelists evaluated the smoothness of each of the compositions of Test Examples that the panelists felt when placing the composition on their palm and applying it to their skin. The compositions were rated according to the following criteria.

A: Nine or more of the ten panelists reported that the smoothness was good.

B: Seven or more and less than nine of the ten panelists reported that the smoothness was good.

BC: Five or more and less than seven of the ten panelists reported that the smoothness was good.

C: Three or more and less than five of the ten panelists reported that the smoothness was good.

D: Less than three of the ten panelists reported that the smoothness was good.

<Non-Powderiness>

Ten experienced panelists evaluated the non-powderiness of each of the compositions of Test Examples that the panelists felt when placing the composition on their palm and applying it to their skin. The compositions were rated according to the following criteria.

A: Nine or more of the ten panelists reported that the non-powderiness was good.

B: Seven or more and less than nine of the ten panelists reported that the non-powderiness was good.

BC: Five or more and less than seven of the ten panelists reported that the non-powderiness was good.

C: Three or more and less than five of the ten panelists reported that the non-powderiness was good.

D: Less than three of the ten panelists reported that the non-powderiness was good.

<Elastic Feel>

Ten experienced panelists evaluated the elastic feel of each of the compositions of Test Examples that the panelists felt when placing the composition on their palm and applying it to their skin. The compositions were rated according to the following criteria.

A: Nine or more of the ten panelists reported that the elastic feel was good.

B: Seven or more and less than nine of the ten panelists reported that the elastic feel was good.

BC: Five or more and less than seven of the ten panelists reported that the elastic feel was good.

C: Three or more and less than five of the ten panelists reported that the elastic feel was good.

D: Less than three of the ten panelists reported that the elastic feel was good.

<Method of Producing Emulsion Cosmetic Containing Elastomer-Coated Inorganic Powder>

The emulsion cosmetic containing an inorganic powder having an elastomer-coated layer of the present invention can be obtained through a step of adding oil phase components and mixing a powder therewith by a homomixer or the like, and a step of emulsifying the resulting oil phase components with aqueous phase components by a homomixer or the like.

Subsequently, the present inventors conducted the investigations on the in-use feel and concealability of an emulsion cosmetic obtained when talc having an elastomer-coated layer as used in the present invention was incorporated in the cosmetic.

TABLE 5

|  |  | Test Example | | | |
| --- | --- | --- | --- | --- | --- |
|  |  | 4-1 | 4-2 | 4-3 | 4-4 |
| Oil phase | Dimethicone (*1) | 27 | 27 | 27 | 27 |
|  | Diphenylsiloxy phenyl trimethicone (*2) | 1 | 1 | 1 | 1 |
|  | Polyglycerin-modified silicone (*3) | 1.5 | 1.5 | 1.5 | 1.5 |
|  | PEG-10 dimethicone (*4) | 2.5 | 2.5 | 2.5 | 2.5 |
|  | Sorbitan sesquiisostearate (*5) | 0.5 | 0.5 | 0.5 | 0.5 |
|  | Octyl methoxycinnamate (*6) | 5 | 5 | 5 | 5 |
|  | (Dimethicone/(PEG-10/15)) crosspolymer (*7) | 4 | 4 | 4 | 4 |
|  | Dimethyldistearylammonium chloride-modified bentonite (*8) | 0.8 | 0.8 | 0.8 | 0.8 |
| Powder | Pigment-grade titanium dioxide (*9) | 6 | 6.5 | 6 | 6 |
|  | Silicone-treated red iron oxide (*10) | 0.53 | 0.53 | 0.53 | 0.53 |
|  | Silicone-treated yellow iron oxide (*11) | 1.37 | 1.37 | 1.37 | 1.37 |
|  | Silicone-treated black iron oxide (*12) | 0.07 | 0.07 | 0.07 | 0.07 |
|  | Particulate titanium dioxide (*13) | 3 | 3 | 3 | 3 |
|  | Nylon powder (*14) | — | — | 0.5 | — |
| Aqueous phase | Elastomer-treated talc | — | — | — | 0.5 |
|  | Ion exchanged water | 36.23 | 35.73 | 35.73 | 35.73 |
|  | Dynamite glycerin | 5 | 5 | 5 | 5 |
|  | Dipropylene glycol | 5 | 5 | 5 | 5 |
|  | Phenoxyethanol | 0.5 | 0.5 | 0.5 | 0.5 |
|  | Total | 100 | 100 | 100 | 100 |
|  | Concealability | BC | B | BC | BC |
|  | Smoothness | B | C | B | B |

TABLE 5-continued

|  | Test Example | | | |
|---|---|---|---|---|
|  | 4-1 | 4-2 | 4-3 | 4-4 |
| Non-powderiness | B | C | B | B |
| Elastic feel | D | D | D | BC |

(*1) Silicone KF-96L-1.5CS (available from Shin-Etsu Chemical Co., Ltd.)
(*2) Silicon KF56 (available from Shin-Etsu Chemical Co., Ltd.)
(*4) Silicone SC9450N (available from Shin-Etsu Chemical Co., Ltd.)
(*5) ESTEMOL 182V (available from The Nisshin OilliO Group, Ltd.)
(*6) Octyl methoxycinnamate (available from Givaudan)
(*7) KSG-210 (available from Shin-Etsu Chemical Co., Ltd.)
(*8) Bentone 38VCG (available from Elementis Specialties Inc.)
(*9) OTS-RC 402P (available from Daito Kasei Kogyo Co., Ltd.)
(*13) Titanium dioxide MT-014V (available from TAYCA CORPORATION)
(*14) Nylon SP-500 (available from NIKKO RICA CORPORATION)
(*15) Elastomer-Treated Talc (Talc JA-68R (A: 2%, B: 3%))

From these Test Examples 4-1 and 4-2, the present inventors found that increasing the amount of the ordinary pigment-grade titanium dioxide to be incorporated improves concealability but yields while residue, resulting in an unnatural finish, and poor in-use feel. In Test Example 4-3, whether a nylon powder improves concealability was investigated, and there was neither a difference in concealability nor an improvement of in-use feel.

On the other hand, in Test Example 4-4, it was found that the use of talc having an elastomer-coated layer results in an improved in-use feel while maintaining the concealability.

Accordingly, the present inventors further conducted an investigation on a nylon powder and talc having an elastomer-coated layer.

TABLE 6

|  |  | Test Example | | |
|---|---|---|---|---|
|  |  | 5-1 | 5-2 | 5-3 |
| Oil phase | Dimethicone (*1) | 27 | 27 | 27 |
|  | Diphenylsiloxy phenyl trimethicone (*2) | 1 | 1 | 1 |
|  | Polyglycerin-modified silicone (*3) | 1.5 | 1.5 | 1.5 |
|  | PEG-10 dimethicone (*4) | 2.5 | 2.5 | 2.5 |
|  | Sorbitan sesquiisostearate (*5) | 0.5 | 0.5 | 0.5 |
|  | Octyl methoxycinnamate (*6) | 5 | 5 | 5 |
|  | (Dimethicone/(PEG-10/15)) crosspolymer (*7) | 4 | 4 | 4 |
|  | Dimethyldistearylammonium chloride-modified bentonite (*8) | 0.8 | 0.8 | 0.8 |
| Powder | Pigment-grade titanium dioxide (*9) | 6 | — | — |
|  | Silicone-treated red iron oxide (*10) | 0.53 | 0.53 | 0.53 |
|  | Silicone-treated yellow iron oxide (*11) | 1.37 | 1.37 | 1.37 |
|  | Silicone-treated black iron oxide (*12) | 0.07 | 0.07 | 0.07 |
|  | Particulate titanium dioxide (*13) | 3 | 3 | 3 |
|  | Nylon powder (*14) | 6 | 10 | 20 |
|  | Elastomer-treated talc | — | — | — |
| Aqueous phase | Ion exchanged water | 30.23 | 32.23 | 22.23 |
|  | Dynamite glycerin | 5 | 5 | 5 |
|  | Dipropylene glycol | 5 | 5 | 5 |
|  | Phenoxyethanol | 0.5 | 0.5 | 0.5 |
| Total |  | 100 | 100 | 100 |
| Concealability |  | B | B | A |
| Smoothness |  | BC | C | C |
| Non-powderiness |  | BC | C | C |
| Elastic feel |  | D | D | D |

As can be understood from Test Examples 5-1 to 5-3, when a nylon powder is used without talc having an elastomer-coated layer (A), the concealability increases but the in-use feel deteriorates.

TABLE 7

|  |  | Test Example | | |
|---|---|---|---|---|
|  |  | 5-4 | 5-5 | 5-6 |
| Oil phase | Dimethicone (*1) | 27 | 27 | 27 |
|  | Diphenylsiloxy phenyl trimethicone (*2) | 1 | 1 | 1 |
|  | Polyglycerin-modified silicone (*3) | 1.5 | 1.5 | 1.5 |
|  | PEG-10 dimethicone (*4) | 2.5 | 2.5 | 2.5 |
|  | Sorbitan sesquiisostearate (*5) | 0.5 | 0.5 | 0.5 |
|  | Octyl methoxycinnamate (*6) | 5 | 5 | 5 |
|  | (Dimethicone/(PEG-10/15)) crosspolymer (*7) | 4 | 4 | 4 |
|  | Dimethyldistearylammonium chloride-modified bentonite (*8) | 0.8 | 0.8 | 0.8 |
| Powder | Pigment-grade titanium dioxide (*9) | 6 | — | — |
|  | Silicone-treated red iron oxide (*10) | 0.53 | 0.53 | 0.53 |
|  | Silicone-treated yellow iron oxide (*11) | 1.37 | 1.37 | 1.37 |
|  | Silicone-treated black iron oxide (*12) | 0.07 | 0.07 | 0.07 |
|  | Particulate titanium dioxide (*13) | 3 | 3 | 3 |
|  | Nylon powder (*14) | — | — | — |
| Aqueous phase | Elastomer-treated talc | 6 | 10 | 20 |
|  | Ion exchanged water | 30.23 | 32.23 | 22.23 |
|  | Dynamite glycerin | 5 | 5 | 5 |
|  | Dipropylene glycol | 5 | 5 | 5 |
|  | Phenoxyethanol | 0.5 | 0.5 | 0.5 |
| Total |  | 100 | 100 | 100 |
| Concealability |  | B | B | A |
| Smoothness |  | B | B | B |
| Non-powderiness |  | B | B | B |
| Elastic feel |  | B | B | B |

As can be understood from Test Examples 5-4 to 5-6, the use of the inorganic powder having an elastomer-coated layer (A) results in a more enhanced in-use feel while improving the conceal ability.

Next, the inventors conducted an investigation on adding talc to an emulsion cosmetic without forming an elastomer-coated layer.

TABLE 8

|  |  | Test Example | | |
|---|---|---|---|---|
|  |  | 6-1 | 6-2 | 6-3 |
| Oil phase | Cyclopentasiloxane (*16) | 15 | 15 | 15 |
|  | Glyceryl tri(2-ethylhexanoate) (*17) | 0 | 0 | 0 |
|  | PEG-10 dimethicon (*18) | 2.5 | 2.5 | 2.5 |
|  | Polysiloxane sesquiisostearate (*19) | 1 | 1 | 1 |
|  | Amino-modified dimethylpolysiloxane (*20) | — | — | 0.2 |
|  | Pyrrolidonecarboxylic acid-modified dimethylpolysiloxane (*21) | — | — | 0.3 |
|  | Elastomer gel | — | 0.5 | — |
|  | Dimethyldistearylammonium chloride-modified bentonite | 0.7 | 0.7 | 0.7 |
| Powder | Pigment-grade titanium dioxide (*9) | 6 | 6 | 6 |
|  | Silicone-treated red iron oxide (*10) | 0.56 | 0.56 | 0.56 |
|  | Silicone-treated yellow iron oxide (*11) | 1.8 | 1.8 | 1.8 |
|  | Silicone-treated black iron oxide (*12) | 0.06 | 0.06 | 0.06 |
|  | Elastomer-treated talc | 10 | — | — |
|  | Untreated talc | — | 9.5 | 9.5 |
| Aqueous phase | Ion exchanged water | 53.88 | 53.88 | 53.88 |
|  | Dynamite glycerin | 3 | 3 | 3 |
|  | Dipropylene glycol | 5 | 5 | 5 |
|  | Phenoxyethanol | 0.5 | 0.5 | 0.5 |
| Total |  | 100 | 100 | 100 |
| Concealability |  | B | B | B |
| Smoothness |  | B | C | C |

TABLE 8-continued

|  | Test Example | | |
|---|---|---|---|
|  | 6-1 | 6-2 | 6-3 |
| Non-powderiness | B | C | C |
| Elastic feel | B | BC | C |

(*16) Execol D5 (available from Shin-Etsu Chemical Co., Ltd.)
(*17) RA-G-308 (available from Nippon Fine Chemical Co., Ltd.)
(*18) Silicone SC9450N (available from Shin-Etsu Chemical Co., Ltd.)
(*19) ESTEMOL 182V (available from The Nisshin OilliO Group, Ltd.)
(*20) Silicone 8004 (available from Shin-Etsu Chemical Co., Ltd.)
(*21) Monasil PCA (available from Croda)

As can be understood from Test Example 6-1, the effects of the present invention cannot be obtained unless talc having an elastomer-coated layer is used.

As can be understood from Test Example 6-2, the intended functions of the present invention cannot be obtained through the steps wherein an elastomer is formed from the elastomer-forming oil components (a1) and (a2), and then a cosmetic is produced.

Also, as can be understood from Test Example 6-3, the intended functions of the present invention cannot be obtained through the steps wherein the elastomer-forming oil components (a1) and (a2) used in the present technology are added together with other oil components, and then a cosmetic is produced.

incorporated is 60% by mass or more in the entirety of oil components of the emulsion cosmetic. An amount less than 60% by mass is not preferable because in this case the effect of improving the in-use feel may not be obtained.

Also, a cosmetic that appears fresh, is smoothly spreadable, and does not have powderiness is obtained when the amount of silicone oil to be incorporated is 50% by mass or more and more preferably 60% by mass or more in the entirety of oil components of the emulsion cosmetic. An amount less than 50% by mass is not preferable because in this case the effect of improving the in-use feel may not be obtained.

TABLE 9

|  |  | Test Example | | | | |
|---|---|---|---|---|---|---|
|  |  | 7-1 | 7-2 | 7-3 | 7-4 | 7-5 |
| Oil phase | Cyclopentasiloxane (*16) | 20 | 15 | 10 | 5 | 5 |
|  | Glyceryl tri(2-ethylhexanoate) (*17) | 10 | 15 | 20 | 25 | 25 |
|  | PEG-10 dimethicon (*18) | 2.5 | 2.5 | 2.5 | 2.5 | 2.5 |
|  | Polysiloxane sesquiisostearate (*19) | 1 | 1 | 1 | 1 | 1 |
|  | Dimethyldistearylammonium chloride-modified bentonite (*22) | 0.7 | 0.7 | 0.7 | 0.7 | 0.7 |
| Powder | Pigment-grade titanium dioxide (*9) | 6 | 6 | 6 | 6 | 6 |
|  | Silicone-treated red iron oxide (*10) | 0.56 | 0.56 | 0.56 | 0.56 | 0.56 |
|  | Silicone-treated yellow iron oxide (*11) | 1.8 | 1.8 | 1.8 | 1.8 | 1.8 |
|  | Silicone-treated black iron oxide (*12) | 0.06 | 0.06 | 0.06 | 0.06 | 0.06 |
|  | Elastomer-treated talc | 6 | 6 | 6 | 6 | — |
|  | Untreated talc | — | — | — | — | 6 |
| Aqueous phase | Ion exchanged water | 42.88 | 42.88 | 42.88 | 42.88 | 42.88 |
|  | Dynamite glycerin | 3 | 3 | 3 | 3 | 3 |
|  | Dipropylene glycol | 5 | 5 | 5 | 5 | 5 |
|  | Phenoxyethanol | 0.5 | 0.5 | 0.5 | 0.5 | 0.5 |
|  | Total | 100 | 100 | 100 | 100 | 100 |
|  | Concealability | B | B | B | B | B |
|  | Smoothness | B | B | B | B | C |
|  | Non-powderiness | B | B | B | B | C |
|  | Elastic feel | B | B | A | A | C |

As can be understood from Test Examples 7-1 to 7-5, a cosmetic that does not have resistance to being spread while yielding an elastic feel and does not have powderiness is obtained when the amount of the polar oil component to be Next, the present inventors conducted an investigation on whether the in-use feel is also improved when an inorganic powder having an elastomer-coated layer other than talc is used.

TABLE 10

| | | Test Example | | | |
|---|---|---|---|---|---|
| | | 8-1 | 8-2 | 8-3 | 8-4 |
| Oil phase | Dimethicone | 27 | 27 | 27 | 27 |
| | Diphenylsiloxy phenyl trimethicone | 1 | 1 | 1 | 1 |
| | Polyglycerin-modified silicone | 1.5 | 1.5 | 1.5 | 1.5 |
| | PEG-10 dimethicone | 2.5 | 2.5 | 2.5 | 2.5 |
| | Sorbitan sesquiisostearate | 0.5 | 0.5 | 0.5 | 0.5 |
| | Octyl methoxycinnamate | 5 | 5 | 5 | 5 |
| | (Dimethicone/(PEG-10/15)) crosspolymer | 4 | 4 | 4 | 4 |
| | Dimethyldistearylammonium chloride-modified bentonite | 0.8 | 0.8 | 0.8 | 0.8 |
| Powder | Pigment-grade titanium oxide | 6 | 6 | 6 | 6 |
| | Silicone-treated red iron oxide | 0.53 | 0.53 | 0.53 | 0.53 |
| | Silicone-treated yellow iron oxide | 1.37 | 1.37 | 1.37 | 1.37 |
| | Silicone-treated black iron oxide | 0.07 | 0.07 | 0.07 | 0.07 |
| | Particulate titanium oxide | 3 | 3 | 3 | 3 |
| | Nylon powder | 2 | 2 | 2 | 2 |
| | Elastomer-treated synthetic phlogopite | 6 | 20 | — | — |
| | Elastomer-treated synthetic phlogopite iron | — | — | 6 | 20 |
| Aqueous phase | Ion exchanged water | 28.23 | 14.23 | 28.23 | 14.23 |
| | Dynamite glycerin | 5 | 5 | 5 | 5 |
| | Dipropylene glycol | 5 | 5 | 5 | 5 |
| | Phenoxyethanol | 0.5 | 0.5 | 0.5 | 0.5 |
| Total | | 100 | 100 | 100 | 100 |
| Concealability | | B | A | B | A |
| Smoothness | | B | B | B | B |
| Non-powderiness | | B | B | B | B |
| Elastic feel | | B | B | B | B |

It was found from Test Examples 8-1 to 8-4 that the in-use feel is also improved when an inorganic powder having an elastomer-coated layer other than talc is used.

What is claimed is:

1. An emulsion cosmetic, comprising:
   (A) 0.5 to 20% by mass of an inorganic powder having an elastomer-coated layer; and
   (B) 20 to 80% by mass of an oil component;
   wherein said elastomer-coated layer comprises:
   (a1) an amino group-containing silicone polymer having structure (1)

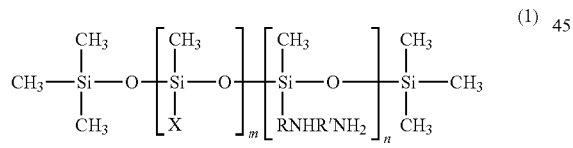

(1)

wherein X is an alkyl group having 1 to 18 carbons, and R and R' are alkyl groups;
and
(a2) a carboxyl group-containing polymer having either structure (2)

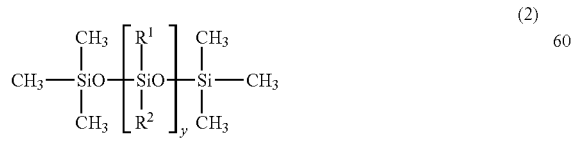

(2)

wherein $R^1$ and $R^2$ are a methyl group or a group represented by formula (4)

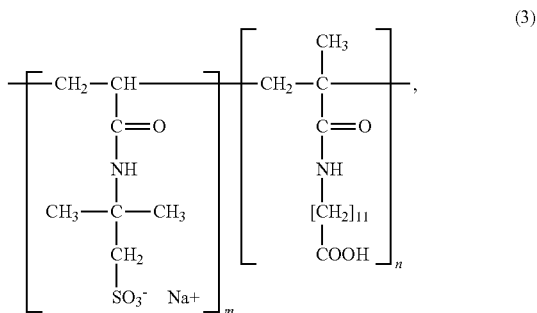

(4)

the total number of said groups $R^1$ and $R^2$ is 1 to 100 per molecule, and y represents an integer of 1 to 50000;
or structure (3)

(3)

wherein the molar ratio (Y/X) between amino groups and carboxyl groups is within the range of 0.1 to 1.2, wherein Y denotes the molar amount of carboxyl groups contained in the component (a2), and X denotes the molar amount of amino groups contained in the component (a1).

2. The emulsion cosmetic, according to claim 1, wherein:
   the amount of the elastomer is 0.5 to 20% by mass relative to the amount of said inorganic powder.

3. The emulsion cosmetic, according to claim 1, wherein:
a silicone oil (b1) accounts for 50% by mass or more of the oil component in the emulsion cosmetic.

4. The emulsion cosmetic, according to claim 3, wherein:
the silicone oil (b1) is one or more selected from chain polysiloxanes and cyclic polysiloxanes.

5. The emulsion cosmetic, according to claim 1, wherein:
a polar oil (b2) accounts for 50% by mass or more of the oil component in the emulsion cosmetic.

6. The emulsion cosmetic, according to claim 5, wherein:
the polar oil (b2) is one or more selected from the group consisting of glyceryl tri(2-ethylhexanoate), pentaerythrityl tetraethylhexanoate, cetyl 2-ethylhexanoate, and isododecyl neopentanoate.

\* \* \* \* \*